United States Patent [19]

Yamaguchi et al.

[11] Patent Number: 5,459,254
[45] Date of Patent: Oct. 17, 1995

[54] PROCESS FOR PREPARING SYNTHETIC INTERMEDIATES OF 2-ALKYNYLADENOSINES AND 2-ALKYNYLADENOSINES

[75] Inventors: Toyofumi Yamaguchi, Hachioji; Takanori Miyashita; Shinji Sakata, both of Choshi; Toichi Abiru, Sawara; Akira Matsuda; Tohru Ueda, both of Sapporo; Kentaro Kogi, Fukushima, all of Japan

[73] Assignees: Yamasa Shoyu Kabushiki Kaisha; Toa Eiyo Ltd., both of Japan

[21] Appl. No.: 149,943

[22] Filed: Nov. 10, 1993

Related U.S. Application Data

[62] Division of Ser. No. 655,354, Apr. 17, 1991, Pat. No. 5,283,327.

[30] Foreign Application Priority Data

Jun. 20, 1989 [JP] Japan ................................ 1-157517
Jan. 13, 1990 [JP] Japan ................................ 2-4727

[51] Int. Cl.$^6$ .................................................. C07H 19/067
[52] U.S. Cl. .................... 536/27.11; 536/27.6; 536/27.62
[58] Field of Search ............................ 536/27.11, 27.61, 536/22.62; 514/46

[56] References Cited

U.S. PATENT DOCUMENTS 4,956,345  9/1990  Miyasaka et al. ......................... 514/46

FOREIGN PATENT DOCUMENTS 0219876  4/1987  European Pat. Off. ................. 514/46
0444196  9/1991  European Pat. Off. ................. 514/46

OTHER PUBLICATIONS

Matsuda et al.(I), "Synthesis and Pharmacological Activities of 2-Alkynyl- and 2-Alkenyladenine Nucleosides," *Nucleic Acids Research Symposium Series*, No. 16, IRL Press Ltd., Oxford, England, 1985, see pp. 97–100.
Matsuda et al. (II), "Introduction of Carbon Substituents at C-2 Position of Purine Nucleosides," *Nucleic Acids Research Symposium Series*, No. 12, IRL Press Ltd., Oxford, England, 1983, see pp. 5–8.
Matsuda et al. (III), "Palladium–Catalyzed Cross–Coupling of 2-Iodoadenosine With Therminal Alkynes: Synthesis and Biological Activities of 2-Alkynyladenosines," *Chem. Phar. Bull.*, 33(4), 19766–1769 (1985).
Kochetkov et al., *Organic Chemistry of Nucleic Acids, Part B*, Plenum Press, New York, 1972, see p. 333.
Nair et al., "Copper Mediated Reactions in Nucleoside Synthesis," *Tett. Lett.*, 31(6), 807–810 (1990).
J. R. M. Scott, Supplementary European Search Report, European Patent Office, Dec. 13, 1991, Appl. No. EP 90 90 9403.

*Primary Examiner*—Douglas W. Robinson
*Assistant Examiner*—L. Eric Crane
*Attorney, Agent, or Firm*—Wenderoth, Lind & Ponack

[57] ABSTRACT

The present invention relates to a novel compound represented by the following formula [I] which is useful as a synthetic intermediate of a 2-alkynyladenosine.

The present invention also relates to a process for producing the compound and a process for producing a 2-alkynyladenosine [IV] by way of the compound.

Further, the present invention relates to a 2-alkynyladenosine derivative represented by the following formula [V] having excellent storage stability and, to a method of storing the 2-alkynyladenosine in the form of that derivative.

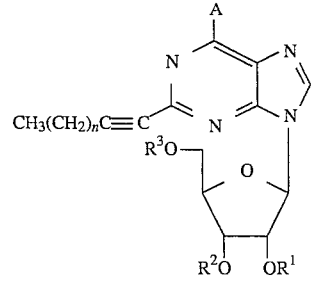

[I] A=a leaving group,

[II] A=$NH_2$,

[V] A=$NHR^4$, wherein $R^1$ through $R^4$ represent a hydrogen atom or a protective group, and n denotes an integer of 1 to 15, provided that $R^1$ through $R^4$ do not represent a hydrogen atom simultaneously.

3 Claims, 1 Drawing Sheet

FIG. 1

PROCESS FOR PREPARING SYNTHETIC INTERMEDIATES OF 2-ALKYNYLADENOSINES AND 2-ALKYNYLADENOSINES

This is a Rule 60 Divisional application of Ser. No. 07/655,354, filed Apr. 17, 1991, U.S. Pat. No. 5,283,327.

FIELD OF THE INVENTION

The present invention relates to a synthetic intermediate suitable for preparing a 2-alkynyladenosine, a process for preparing the synthetic intermediate, a process for preparing a 2-alkynyladenosine utilizing the synthetic intermediate and a stable 2-alkynyladenosine derivative.

BACKGROUND OF THE INVENTION

2-alkynyladenosines are compounds which have an antihypertensive effect and are expected to be developed as medical agents (see Japanese Patent Laid-Open Publication Nos. 99330/1987 and 99395/1987, EP 0219876 A2 and the like).

However, when 2-alkynyladenosines are intended to be developed as medical agents, they have problems in production and storage described in detail below:

I. Problems in production

As a process for preparing a 2-alkynyladenosine, there has hitherto been reported only the method by Matsuda et al. which comprises reacting 6-chloro-2-iodo-9-(2,3,5-tri-O-acetyl-β-D-ribofuranosyl)purine with methanolic ammonia in a sealed tube at 60° C. for 17 hours to form 2-iodoadenosine (this step being referred to hereinafter as "amination step", in which the deprotection of the acetyl group is simultaneously conducted), and reacting the 2-iodoadenosine thus obtained with an alkyne in the presence of bis-(triphenylphosphine)palladium dichloride and cuprous iodide at 80° C. for 1 hour or more to obtain a 2-alkynyladenosine (this step being referred to hereinafter as "cross-coupling step") [see Nucleic Acids Research, Symposium Series No. 12, pp. 5–8 (1983); Chem. Pharm. Bull., 33 (4), pp. 1766–1769 (1985); Nucleic Acids Research, Symposium Series No. 16, pp. 97–100 (1985); NUCLOSIDES & NUCLEOTIDES, 6 (1 & 2), pp. 85–94 (1987); etc.].

The reaction scheme of the method by Matsuda et al. is represented by the following structural formulas:

wherein Ac represents an acetyl group, and n denotes an integer of 1 to 15.

Although the method by Matsuda et al. is a very excellent method as a process for preparing a 2-alkynyladenosine, it has had the following problems to be solved and thus has not been necessarily a completely satisfactory method.

(1) Problems in the amination step (i) The reaction in the amination step described above does not proceed smoothly at room temperature and thus is required to be conducted at an elevated temperature while the evaporation of methanolic ammonia is prevented, so that it is essential therefor to use a pressure vessel such as a sealed tube or the like. However, such a pressure vessel has been economically problematic because it is expensive and further always has the risk of explosion.

(ii) In the aforementioned amination step, a large amount of by-products such as acetamide and ammonium chloride are produced in addition to 2-iodoadenosine as the object compound, and it has been very difficult to separate the 2-iodoadenosine from these by-products.

(2) Problems in the cross-coupling step (i) In the aforementioned cross-coupling step, cuprous iodide is added to the reaction solution in order to promote and complete the reaction in the proportion of about 0.06 mole to 1 mole of 2-iodoadenosine. Therefore, a large amount of copper compounds are introduced as contaminants into the crude reaction product, and treatment with hydrogen sulfide is essential for removing the copper compounds. Hydrogen sulfide is, however, a dangerous substance which has toxicity and an ill smell and is difficult to handle. Moreover it has been extremely difficult to remove completely the copper compounds from the reaction product by the treatment with hydrogen sulfide.

(ii) The reaction solution obtained after the aforementioned cross-coupling step exhibits a dark brown color, and it has been extremely difficult to remove completely colored materials from the reaction product.

(iii) The waste or waste fluid after the reaction contains a large amount of the copper compounds, and it is necessary to remove the copper compounds from the waste in order to avoid environmental pollution.

II. Problems in storage

A 2-alkynyladenosine is a compound which is devoid of storage stability. For example, from the result of a severe test (conducted for three months under the storage conditions of a temperature of 40° C. and a relative humidity of 75%), the residual rate of a 2-alkynyladenosine is about 70%. Thus, a 2-alkynyladenosine cannot have a scale merit of its being prepared in a large amount and being stored until it is demanded for use, and it has been necessary to prepare it in a small amount just before its use. When a 2-alkynyladenosine is to be synthesized in a large amount, a special device which can control the temperature and humidity for storing it has been required.

Accordingly, an object of the present invention, in one aspect thereof, is to establish a novel process for preparing a 2-alkynyladenosine wherein the aforementioned problems of production have been solved.

Another object of the present invention is to provide a 2-alkynyladenosine derivative which has excellent storage stability.

Other objects of the present invention will be apparent from the following description.

SUMMARY OF THE INVENTION

The present inventors have conducted extensive research on the solution of the aforementioned problems of the production and storage of a 2-alkynyladenosine for the development thereof as a medical agent. As a result, they have made the unexpected discovery, first, that the problems of production in the aforementioned conventional method by Matsuda et al. can be solved by reversing the order of "the amination step" and "the cross-coupling step" in the conventional method.

The present inventors have also found that a 2-alkynylpurine ribofuranoside derivative represented by the following formula [I]:

wherein Y represents a leaving group, n denotes an integer of 1 to 15, and $R^1$, $R^2$, and $R^3$ represent a hydrogen atom or a protective group, is extremely useful as a synthetic intermediate of 2-alkynyladenosine.

Furthermore, they have found with respect to the problems of storage that a derivative of 2-alkynyladenosine having a protective group which is ordinarily used for the protection of an amino group introduced into an amino group at the 6 position and/or a protective group which is ordinarily used for the protection of a hydroxyl group introduced into at least one of the hydroxyl groups at the 2', 3' and 5' positions has excellent storage stability.

Thus, the present invention has been achieved primarily on the basis of these findings.

Accordingly, the present invention relates to a novel 2-alkynylpurine ribofuranoside derivative represented by the above formula [I].

Furthermore, the present invention relates to a process for preparing a 2-alkynylpurine ribofuranoside derivative represented by the above formula [I], which process comprises reacting a compound represented by the following formula [II]:

wherein X represents a bromine atom or an iodine atom, and $R^1$, $R^2$, $R^3$, and Y are as defined above, with an alkyne represented by the following formula [III]:

$$HC{\equiv}C(CH_2)_nCH_3 \qquad [III]$$

wherein n is as defined above, in a reaction solvent in the presence of a palladium catalyst or in the presence of a palladium catalyst and trace amounts of a copper compound.

The present invention also relates to a process for preparing a 2-alkynyladenosine represented by the following formula [IV]:

wherein n is as defined above, which process comprises reacting a 2-alkynylpurine ribofuranoside derivative represented by the above formula [I] with an aminating agent and then removing the protective groups, or removing the protective groups simultaneously with the reaction with the aminating agent.

Further, the present invention relates to a process for preparing a 2-alkynyladenosine represented by the above formula [IV], which process comprises reacting a compound represented by the above formula [II] with an alkyne represented by the above formula [III] in a reaction solvent in the presence of a palladium catalyst or in the presence of a palladium catalyst and trace amounts of a copper compound to produce a compound represented by the above formula [I], then reacting the resulting compound with an aminating agent and removing the protective groups, or removing the protective groups simultaneously with the-reaction with the aminating agent.

Furthermore, the present invention relates to a 2-alkynyladenosine derivative represented by the following formula [V]:

wherein $R^1$ through $R^4$ represent a hydrogen atom or a protective group, at least one of $R^1$ through $R^4$ being a protective group, and n is as defined above, and to a method of storing the 2-alkynyladenosine in this form utilizing the storage stability of the derivative.

DESCRIPTION OF THE FIGURE

In the drawing, the single FIGURE is a graph indicating the hypotensive effects of 2-(1-octynyl)adenosine and 2-(1-octynyl)-9-(2,3,5-tri-O-acetyl-β -D-ribofuranosyl)adenine which have excellent storage stability. In the figure, the symbols ○ and ● refer to 2-(1-octynyl)adenosine, and △ and ▲ refer to 2-( 1-octynyl)-9-(2,3,5-tri-O-acetyl-β-D-ribofuranosyl)adenine, in which ○ and △ show the result on the dose of 0.3 mg/kg, and ● and ▲ show the result on the dose of 1.0 mg/kg.

DESCRIPTION OF THE PREFERRED EMBODIMENTS

I. Synthetic intermediate of a 2-alkynyladenosine, a process for preparing the synthetic intermediate, and a process for preparing the 2-alkynyladenosine utilizing the synthetic intermediate:

The compound useful as a synthetic intermediate of 2-alkynyladenosine is a compound represented by the above formula [I] (the compound of the formula [I] may be referred to hereinafter as "the synthetic intermediate of the present invention") In the formula, $R^1$, $R^2$, and $R^3$, Y and n are as defined above. Specifically, as the protective groups represented by $R^1$, $R^2$, and $R^3$, there are no particular limitations provided that they are those which are ordinarily used as the protective groups of the hydroxyl group of a nucleoside. For example, there is an acyl group represented by the following formula [VI]:

[VI]

wherein $R^5$ represents a hydrogen atom, an alkyl group, a cycloalkyl group, an aralkyl group or an aryl group.

Specific examples of the alkyl group represented by the symbol $R^5$ are straight or branched alkyl groups having 1 to 10 carbon atoms, more specific examples being methyl, ethyl, propyl, isopropyl, butyl, isobutyl, secbutyl, tert-butyl, pentyl, isopentyl, neopentyl, hexyl, isohexyl, heptyl, octyl, nonyl, and decyl.

The cycloalkyl group is a cyclic alkyl group having 3 to 10 carbon atoms, specific examples being cyclopropyl, cyclobutyl, cyclopentyl, cyclohexyl, and adamantyl.

The aralkyl group is a substituted or unsubstituted aralkyl group, specific examples being benzyl, 1-phenylethyl, methylbenzyl, fluorobenzyl, chlorobenzyl, methoxybenzyl, dimethoxybenzyl, nitrobenzyl, phenethyl, picolyl, and 3-indomethyl.

Specific examples of the aryl group are substituted or unsubstituted aryl groups, more specific examples being phenyl, tolyl, xylyl, mesityl , cumenyl, ethylphenyl, fluorophenyl, chlorophenyl, bromophenyl, methoxyphenyl, dimethoxyphenyl, ethoxyphenyl, diethoxyphenyl, propoxyphenyl, methylenedioxyphenyl, nitrophenyl, cyanophenyl, acetylphenyl, carbamoylphenyl, methoxycarbonylphenyl, naphthyl, thienyl, and pyrrolyl.

Also, in addition to the above-described acyl groups, there are alkoxymethyl groups such as methoxymethyl, ethoxymethyl, and propoxymethyl; aralkyl groups such as triphenylmethyl , p-methoxyphenyldiphenylmethyl, and α-naphthyldiphenylmethyl; pyranyl groups such as tetrahydropyran-2-yl and 4-methoxytetrahydropyran-4-yl; silyl groups such as trimethylsilyl, triethylsilyl, isopropyldimethylsilyl, tert-butyldimethylsilyl, methyldi-tert-butylsilyl, triisopropylsilyl, and tetraisopropyldisiloxanyl; acetal or ketal type protective groups such as ethylidene, propylidene, isopropylidene, benzylidene, cyclohexylidene, cyclopentylidene, methoxymethylidene, ethoxymethylidene, and dimethoxymethylidene; and alkoxycarbonyl groups such as methoxycarbonyl, ethoxycarbonyl, and tertbutoxycarbonyl.

The leaving groups represented by Y are not particularly limited provided that they are groups which have low reactivity with an alkyne and can be easily substituted by an amino group by the reaction with an aminating agent such as ammonia. Specific examples are arylsulfonyloxy groups such as benzenesulfonyloxy, p-toluenesulfonyloxy, mesitylenesulfonyloxy, and 2,4,6-triisopropylbenzenesulfonyloxy and a chlorine atom.

Such synthetic intermediates of the present invention can be prepared by the so-called cross-coupling reaction which comprises reacting a compound represented by the above formula [II] with an alkyne represented by the above formula [III] in a reaction solvent in the presence of a palladium catalyst.

In the compounds represented by the formula [II] as starting compounds, $R^1$, $R^2$, $R^3$, and Y are the same as those of the synthetic intermediates of the present invention. Also, X represents an iodine atom or a bromine atom, and a compound represented by the formula [II] in which X represents an iodine atom having a high reactivity with an alkyne is preferably used.

For the alkyne represented by the formula [III], one which has n corresponding to the alkynyl portion of the objective compound for synthesis may be appropriately used.

As the reaction solvent, a basic solvent such as triethylamine, tributylamine, N,N-diisopropylethylamine, trioctylamine, N,N,N',N'-tetramethyl-1,8-naphthalenediamine, dimethylaniline, diethylaniline, or pyridine, alone or in admixture with a aprotic polar solvent such as acetonitrile, N,N-dimethylformamide, dimethylsulfoxide, N,N-dimethylacetamide, tetrahydrofuran, or 1,4-dioxane can be used.

As the palladium catalyst, his (acetonitrile)palladium dichloride, his (triphenylphosphine )palladium dichloride, bis(benzonitrile)palladium dichloride, tetrakis(triphenylphosphine)palladium, bis(triphenylphosphine)palladium diacetate or the like can be used. As for some of the aforementioned palladium catalysts, such as bis(triphenylphosphine)palladium dichloride or bis(triphenylphosphine)palladium diacetate, the products obtained by reacting in situ palladium dichloride or palladium diacetate with triphenylphosphine in the reaction solution may be used directly.

The amount of the palladium catalyst used is in the so-called catalyst amount, i.e., in the range of 0.001– 0.1 mole to 1 mole of the starting compound represented by the formula [II].

A copper compound in addition to the palladium catalyst may be added to the reaction solution in order to promote the cross-coupling reaction. For example, a copper halide compound such as cuprous iodide or cuprous bromide may be added to the reaction solution in trace amounts of 0.001–0.02 mole per 1 mole of the compound represented by the formula [II].

The reaction of a starting compound and an alkyne can be carried out by reacting 1 to 2 moles of the alkyne with 1 mole of the starting compound in the presence of a palladium catalyst or both a palladium catalyst and a copper compound at a reaction temperature of 10° to 90° C. for 1 to 100 hours.

In this connection, when an alkyne represented by the above formula [III] wherein n =9 or more is used, it is essential to increase the amount of the palladium catalyst used, or to use a combination of a palladium catalyst and a copper compound.

After completing the reaction, the synthetic intermediate of the present invention thus obtained is, if necessary, subjected to isolation and purification process ordinarily used for nucleosides, such as adsorption chromatography or recrystallization, and in the case where a copper compound has been added to the reaction solution, the extraction and distribution treatment with an organic solvent-water is carried out, and the synthetic intermediate is supplied to the succeeding amination step for preparing an 2-alkynyladenosine.

As the organic solvent used for the extraction and distribution treatment with an organic solvent-water, a carboxylic acid ester such as ethyl acetate or ethyl propionate, or a hydrocarbon such as benzene or toluene can be used. The mixing ratio of the organic solvent and water is not specifically limited, and a metal chelating agent such as EDTA (ethylenediaminetetraacetic acid) may be added to the solvent mixture of the organic solvent-water.

Examples of the aminating agent used for the reaction for preparing a 2-alkynyladenosine from the synthetic intermediate of the present invention are liquid ammonia, alcoholic ammonias such as methanolic ammonia and ethanolic ammonia, and mixtures of organic solvents such as acetonitrile, 1,2-dimethoxyethane, 1,4-dioxane, and tetrahydrofuran with aqueous ammonia.

The amination reaction can be carried out by reacting the synthetic intermediate of the present invention with the aforementioned aminating agent at room temperature to 100° C. for 2 hours to 2 weeks.

After the reaction, the 2-alkynyladenosine can be obtained by deprotection, if necessary, and then by isolation and purification by an ordinary method.

When an acyl group is used as a protective group, the acyl group is simultaneously removed with the reaction of the synthetic intermediate of the present invention and the aminating agent, and thus deprotection after the reaction is not necessary in such a case.

The process for preparing a 2-alkynyladenosine of the present invention as described above has the features shown in Table 1 as compared with the conventional method by Matsuda et al.

TABLE 1

| Item | Present Process | Conventional Process |
| --- | --- | --- |
| (1) Reaction order | cross-coupling step → amination | amination step → cross-coupling |

TABLE 1-continued

| Item | Present Process | Conventional Process |
| --- | --- | --- |
| (2) Amination step | step | step |
| (i) Pressure vessel | not required | required |
| (ii) Isolation of reaction products | easy | difficult |
| (3) Cross-coupling step | | |
| (i) Use of copper compound | nonessential | essential |
| (ii) Color of reaction solution after reaction | pale brown - brown (transparent) | dark brown (not transparent) |
| (iii) Method for removing copper compound | extraction and distribution treatment with organic solvent - water | treatment with hydrogen sulfide |
| (iv) Operability of removing copper compound | easy | difficult |

The following features (i), (ii), and (iii) are worthy of special mention as compared with those of the conventional method by Matsuda et al.:

(i) The objective reaction product is easily isolated after the amination step.

In the amination step of the conventional method, by-products such as acetamide and ammonium chloride are produced in addition to 2-iodoadenosine, and it is difficult to separate these by-products from 2-iodoadenosine. In contrast, according to the process of the present invention, the reaction product after the amination step is a 2-alkylyladenosine, and by-products such as acetamide and ammonium chloride are produced in a manner similar to that of the conventional method when an acetyl group is used as a protective group. However, it is comparatively easy to separate the by-products from the 2-alkynyladenosine.

(ii) The addition of the copper compound is not essential in the cross-coupling step, it being sufficient that the amount of the compound, if it is needed, is ⅓ or less of the amount necessitated in the conventional method.

Therefore, the dark brown coloration of the reaction solution which is believed to be caused by the presence of the copper compound can be suppressed, and the colored materials and the reaction product are easily separated from each other.

Also, even if the copper compound is added to the reaction solution, it is added only in trace amounts, and thus treatment with hydrogen sulfide is not necessary. Copper ions can be easily removed from the reaction product by the extraction and distribution treatment with an organic solvent-water, and the copper compounds can also be easily removed from the waste or waste fluid.

(iii) The reaction temperature in the cross-coupling step can be lowered.

When a compound represented by the aforementioned formula [II] wherein Y is a chlorine atom is used as a starting compound, it is possible to conduct the reaction at a temperature of 60° C. or less, which is lower than the reaction temperature of 80° C. in the conventional method, and particularly at a temperature of 40° C. or less in the presence of both the palladium catalyst and the copper compound. Thus, it is possible to avoid the cross-coupling reaction at an elevated temperature which may cause dark brown coloration of the reaction solution as in the conventional method, and the dark brown coloration of the reaction solution can be suppressed more effectively.

In this connection, the reaction temperature in the process of the present invention is such that if the conventional cross-coupling reaction is conducted at that reaction temperature, the reaction will not be completed, and the yield of the 2-alkynyladenosine will decrease greatly.

The process for preparing a 2-alkynyladenosine of the present invention comprising the reaction steps having the aforementioned advantages is simple and safe and moreover economic. Therefore, it is extremely useful for the production of 2-alkynyladenosines.

Example I-1

(i) In 10.5 ml of N,N-dimethylformamide were suspended 3.23 g (6 mmole) of 9-(2,3,5-tri-O-acetyl-β-D-ribofuranosyl)- 6-chloro-2-iodopurine, 157 mg (0.6 mmole) of triphenylphosphine and 53 mg (0.3 mmole) of palladium chloride, and 1.67 ml of triethylamine and 0.66 ml of 1-pentyne were added to the suspension. The mixture was stirred and caused to react at 50° C. for 6 hours. The solution after the reaction had a transparent brown color, which was obviously paler than the dark brown of the reaction solution obtained in the cross-coupling step of the conventional method by Matsuda et al. which was not transparent. The reaction solution was then concentrated, and 200 ml of ethyl acetate was added to the residue to obtain a solution, which was washed several times with a saturated brine solution. After the organic layer was concentrated, the residue was subjected to silica gel column chromatography (eluent: chloroform:methanol =10 to 5:1 (v/v)) to remove colored materials and other by-products, and 2.36 g (yield 82%) of 9-(2,3,5-tri-O-acetyl-β-D-ribofuranosyl)-6-chloro-2-( 1-pentynyl)purine was obtained as a viscous material.

$^1$H-NMR (CDCl$_3$) δ(ppm):

1.07 (3H, t, CH$_3$), 1.71 (2H, m, CH$_2$), 2.08 (3H, s, acetyl), 2.16 (6H, s, acetyl×2), 2.49 (2H, t, CH$_2$C≡C), 4.40–4.50 (3H, m, H-4', H-5'), 5.57 (1H, dd, H-3'), 5.80 (1H, dd, H-2'), 6.32 (1H, d, H-1'), 8.31 (1H, s, H-8)

UV (methanol): λ$_{max}$ 268, 284 nm (ii) The procedure in (i) was repeated with 1.2 equivalent of 1-octyne in place of 1-pentyne to obtain 2.88 g (yield 92%) of 9-(2,3,5-tri-O-acetyl-β-D-ribofuranosyl)- 6-chloro-2-(1-octynyl)purine as a viscous material. The solution after the reaction in this case also had a brown color.

$^1$H-NMR (CDCl$_3$) δ(ppm):

0.90 (3H, t, CH$_3$), 1.28–1.74 (8H, m, CH$_2$×4), 2.08 (3H, s, acetyl), 2.17 (6H, s, acetyl×2), 2.49 (2H, t, CH$_2$C≡C), 4.40–4.50 (3H, m, H-4', H-5'), 5.57 (1H, dd, H-3'), 5.80 (1H, dd, H-2'), 6.33 (1H, d, H-1'), 8.31 (1H, s, H-8)

UV (methanol): λ$_{max}$ 268, 282 nm (iii) In 12 ml of 1,4-dioxane were suspended 2.15 g (4 mmole ) of 9-(2,3,5-tri-O-acetyl-β-D-ribofuranosyl)-6- chloro-2-iodopurine , 56 mg (0.08 mmole) of bis(triphenylphosphine)palladium dichloride and 15 mg (0.08 mmole ) of cuprous iodide, and 1.2 ml of triethylamine and 0.75 ml of 1-nonyne were added to the suspension. The mixture was stirred and caused to react at room temperature (25° C.) for 12 hours. The reaction solution at this time had a transparent pale brown color, which was paler than those in the aforementioned (i) or (ii). After the reaction, the solution was concentrated, and 200 ml of ethyl acetate was added to the residue to obtain a solution, which was distributed and washed several times with an aqueous EDTA.2Na solution and a saturated brine solution, respectively to remove copper ions. The organic layer was subjected to silica gel column chromatography in the same manner as in (i) to remove colored materials and other by-products and to produce 1.90 g (yield 89%) of 9-(2,3,5-tri-O-acetyl-β-D-ribofuranosyl)- 6-chloro-2-(1-nonynyl)purine as a viscous material.

$^1$H-NMR (CDCl$_3$) δ(ppm):

0.89 (3H, t, CH$_3$), 1.24–1.74 (10H, m, CH$_2$×5), 2.08 (3H, s, acetyl), 2.16 (6H, s, acetyl×2), 2.48 (2H, t, CH$_2$C≡C), 4.40–4.50 (3H, m, H-4', H-5'), 5.58 (1H, dd, H-3'), 5.80 (1H, dd, H-2'), 6.32 (1H, d, H-1'), 8.31 (1H, s, H-8)

UV (methanol): λ$_{max}$ 268, 284 nm

Example I-2

To 4 mmole of each of the compounds obtained in Example I-1 was added 45 ml of 1,4-dioxane-concentrated aqueous ammonia (2:1, v/v), and the mixture was stirred and heated at 50° C. for 2 days to conduct amination and simultaneously to deprotect the acetyl group to obtain a 2-alkynyladenosine. After the reaction, the solution was concentrated and subjected to silica gel column chromatography (eluent: chloroform:methanol=10 to 5:1, v/v) to separate the 2-alkynyladenosine from other by-products. The 2-alkynyladenosine obtained was recrystallized from methanol-water. The 2-alkynyladenosine was successfully separated with ease from other by-products by silica gel column chromatography.

| Compound | Output | Yield |
| --- | --- | --- |
| 2-(1-pentynyl)adenosine | 1.00 g | 75% |
| 2-(1-octynyl)adenosine | 1.22 g | 81% |
| 2-(1-nonynyl)adenosine | 1.24 g | 80% |

Example I-3

In 20 ml of 1,4-dioxane were suspended 2.01 g (3 mmole) of 9-(2,3,5-tri-O-acetyl-β-D-ribofuranosyl)-2-iodo-6 -O-p-toluenesulfonylhypoxanthine, 105 mg (0.15 mmole) of bis-(triphenylphosphine)palladium dichloride and 12 mg (0.06 mmole) of cuprous iodide, and 1 ml of N,N-diisopropylethylamine and 0.65 ml of 1-octyne were added to the suspension. The mixture was stirred and caused to react at 80° C. for 10 hours. The solution after the reaction had a transparent brown color. After the reaction, the treatment in the same manner as in Example I-1-(iii) gave 1.50 g (yield 76%) of 9-(2,3,5-tri-O-acetyl-β -D-ribofuranosyl)-2-(1-octynyl)-6-O-p-toluenesulfonylhypoxanthine as a viscous material.

1H-NMR (CDCl$_3$) δ(ppm):

0.93 (3H, t, methyl), 1.28–1.74 (8H, m, CH$_2$×4), 2.06 (3H, s, acetyl), 2.15 (6H, s, acetyl×2), 2.47–2.51 (5H, m, p-methyl, CH$_2$C≡C), 4.38–4.50 (3H, m, H-4', H-5'), 5.55 (1H, dd, H-3'), 5.78 (1H, dd, H-2'), 6.30 (1H, d, H-1'), 7.37 (2H, d, aromatic H), 8.13 (2H, d, aromatic H), 8.23 (1H, s, H-8)

Example I-4

To 800 mg of 9-(2,3,5-tri-O-acetyl-β-D-ribofuranosyl)- 2-(1-octynyl)-6-O-p-toluenesulfonyl-hypoxanthine obtained in Example I-3 was added 100 ml of a solution of ammonia in tetrahydrofuran (saturated at 0° C.) to form a solution, which was caused to react at room temperature for 3 days to produce 9-(2,3,5-tri-O-acetyl-β-D-ribofuranosyl)-2-(1-octynyl)adenine. The reaction solution was then concentrated, and the residue obtained was dissolved in 50 ml of methanolic ammonia (saturated at 0° C.). The mixture was caused to react at room temperature for 2 days to deprotect the acetyl group. The reaction solution was concentrated and then purified by silica gel column chromatography (eluent: chloroform:methanol =10 to 5:1, v/v) and crystallized from methanol water to obtain 305 mg (yield 67%) of 2-(1-octynyl)adenosine.

Reference Example 1

Synthesis of 9-(2,3,5-tri-O-acetyl-β-D-ribofuranosyl)-2-iodo-6 -O-p-toluenesulfonylhypoxanthine:

In 100 ml of acetonitrile was dissolved 8.6 g of 9-( 2,3,5-tri-O-acetyl-β-D-ribofuranosyl)-6-O-p-toluenesulfonylguanine synthesized according to the method By Daskalov et al. [Bull. Chem. Soc. Jpn., 54 (10), 3076–3083 (1981)]. To the solution were added 3.3 g of cuprous iodide, 8.3 g of iodine, 7.5 ml of diiodomethane and 10 ml of isoamyl nitrite. The mixture was stirred at 70° C. for 30 minutes.

The reaction solution was cooled and then concentrated, and the residue obtained was dissolved in chloroform. The chloroform solution was washed with an aqueous sodium thiosulfate solution, dried over anhydrous sodium sulfate and concentrated to dryness. The residue thus obtained was purified by silica gel column chromatography to produce 4.95 g (yield 48%) of 9-(2,3,5-tri-O-acetyl-β -D-ribofuranosyl)-2-iodo-6-O-p-toluenesulfonylhypoxanthine in the form of foam.

$^1$H-NMR (CDCl$_3$) δ(ppm):

2.09, 2.13, 2.17 (3H, s, acetyl), 2.48 (3H, s, p-CH$_3$), 4.39–4.46 (3H, m, H-4', H-5'), 5.57 (1H, dd, H-3'), 5.76 (1H, dd, H-2'), 6.18 (1H, d, H-1'), 7.41 (2H, d, aromatic H), 8.12 (2H, d, aromatic H), 8.13 (1H, s, H-8)

Reference Example 2

Synthesis of 2-alkynyladenosine according to the conventional method by Matsuda et al.:

(i) To 30 ml of methanolic ammonia (saturated at 0° C.) was added 3.23 g (6 mmole) of 6-chloro-2-iodo-9-( 2,3,5-tri-O-acetyl-β-D-ribofuranosyl)purine, and the mixture was caused to react in a sealed tube at 60° C. for 17 hours. After the reaction, the solution was cooled and concentrated under reduced pressure. In the residue thus obtained, by-products such a acetamide and ammonium chloride were contained in addition to 2-iodoadenosine. In order to remove these by-products, purification of the 2-iodoadenosine by silica gel column chromatography (eluent: chloroform:methanol =10 to 5:1, v/v) was attempted, but the 2-iodoadenosine could not completely be separated from acetamide because of the very close retention times of the two compounds.

(ii) In 130 ml of a solvent mixture of dimethylformamide-triethylamine (10:3) was dissolved 3.93 g (10 mmole) of 2-iodoadenosine. 210 mg of bis(triphenylphosphine)palladium dichloride and 120 mg of cuprous iodide were added to the solution, and then 1.62 ml (1.1 equivalent) of 1-octyne was added thereto in a stream of argon. The reaction was conducted at 80° C. for 3 hours. The solution after the reaction had a dark brown color and was not transparent.

The reaction solution was concentrated under reduced pressure. The residue obtained could not be easily dissolved in a carboxylic acid ester such as ethyl acetate nor in a hydrocarbon such as benzene, and the method for removing copper compounds by the extraction and distribution treatment with an organic solvent-water which is applicable to the present invention could not be applied to this case.

Accordingly, hydrogen sulfide was passed through the solution in a conventional manner, the precipitate (mainly comprising copper sulfide) formed was removed, and the solution was further concentrated. The residue was subjected to silica gel column chromatography in order to purify crude 2-(1-octynyl)adenosine. However, colored materials could not be removed completely from the 2-(1-octynyl)adenosine.

II. Stable 2-alkynyladenosine derivatives and the use thereof:

A 2-alkynyladenosine derivative having storage stability is represented by the above formula [V] (sometimes referred to hereinafter as "derivative of the present invention"). In the formula, R$^1$ through R$^4$ are as defined above. As the protective groups of the hydroxyl group which are represented by R$^1$, R$^2$, and R$^3$, those which are ordinarily used for the protection of a hydroxyl group are sufficient and are not specifically limited, an acyl group being preferred. As the protective group of an amino group which is represented by R$^4$, those which are ordinarily used for the protection of an amino group are sufficient and are not specifically limited, an acyl group being preferred. As the acyl group, the examples mentioned for R$^1$, R$^2$, and R$^3$ in the formula [I] can be used.

Among the compounds of the formula [V], those in which R$^4$ represents a hydrogen atom may be in the form of salt. Specific examples of such salt include acid addition salts with inorganic acids such as hydrochloric acid and sulfuric acid, and with organic acids such as citric acid and p-toluenesulfonic acid.

The storage stability of the aforementioned 2-alkynyladenosine derivatives is described below with respect to Test Examples.

Test Example 1

The test compounds shown in Table 2 below were stored at a temperature of 40° C. and a relative humidity of 75% under a light shielding condition.

After storage for 3 months, the residual rate of the test compounds was measured by HPLC.

TABLE 2

| Test Compound | Structure of Compound of the Formula [V] | | | | Residual Rate (%) | Analytical Conditions |
|---|---|---|---|---|---|---|
| | n | R$^4$ | R$^1$ | R$^2$ | R$^3$ | | |
| Derivative of the present invention | 3 | hydrogen | acetyl | acetyl | acetyl | 100 | (1) |
| | 5 | hydrogen | acetyl | acetyl | acetyl | 100 | (1) |
| | 6 | hydrogen | acetyl | acetyl | acetyl | 100 | (1) |
| | 13 | hydrogen | acetyl | acetyl | acetyl | 99.7 | (2) |
| | 5 | hydrogen | propionyl | propionyl | propionyl | 99.8 | (1) |

TABLE 2-continued

| Test Compound | Structure of Compound of the Formula [V] | | | | | Residual Rate (%) | Analytical Conditions |
|---|---|---|---|---|---|---|---|
| | n | $R^4$ | $R^1$ | $R^2$ | $R^3$ | | |
| | 5 | butyryl | hydrogen | hydrogen | hydrogen | 99.6 | (3) |
| Control | 5 | hydrogen | hydrogen | hydrogen | hydrogen | 67.8 | (4) |
| | 6 | hydrogen | hydrogen | hydrogen | hydrogen | 70.9 | (4) |

Analytical conditions:
(1)
 Column: Hitachi #3056
 Detection: 270 nm
 Solvent: 60% acetonitrile-0.05M triethylammonium acetate buffer (TEAA) (pH 7.0)
(2)
 Column: Hitachi #3056
 Detection: 270 nm
 Solvent: 95% methanol-0.05M TEAA (pH 7.0)
(3)
 Column: TSK gel ODS-80TM (manufactured by TOSO K.K.)
 Detection: 270 nm
 Solvent: 50% acetonitrile-0.05M TEAA (pH 7.0)
(4)
 Column: TSK gel ODS-80TM
 Detection: 270 nm
 Solvent: 40% acetonitrile-0.05M TEAA (pH 7.0)

As shown in Table 2, the derivatives of the present invention are extremely stable as compared with the 2-alkynyladenosines, and thus the compounds in this form can be utilized for storing the 2-alkynyladenosines.

Among the derivatives of the present invention, those in which $R^1$, $R^2$, and $R^3$ represent an acetyl group, and $R^4$ represents a hydrogen atom have not only storage stability but also hypotensive effect at the same level as the 2-alkynyladenosines, as will be apparent from the results of the following physiological activity tests, and thus they are expected to be developed as medical agents.

Test Example 2

Effect of the test compounds on the blood pressure in SHR ( noninvasive measurement ):

To 12 to 15 week-old male SHRs ( 5 animals per group ), a sample, 2-(1-octynyl)adenosine or 2-(1-octynyl)- 9- ( 2,3,5-tri-O-acetyl-β-D-ribofuranosyl)adenine, which had been suspended in a 0.5% CMC (carboxymethylcellulose)/ physiological saline solution was administered orally. The blood pressure of SHR was measured with a tail artery sphygmomanometer (manufactured by Nalco Co., Model PE-300) prior to administration and at 1 hour, 2 hours, 4 hours and 6 hours after administration.

Figure 1:
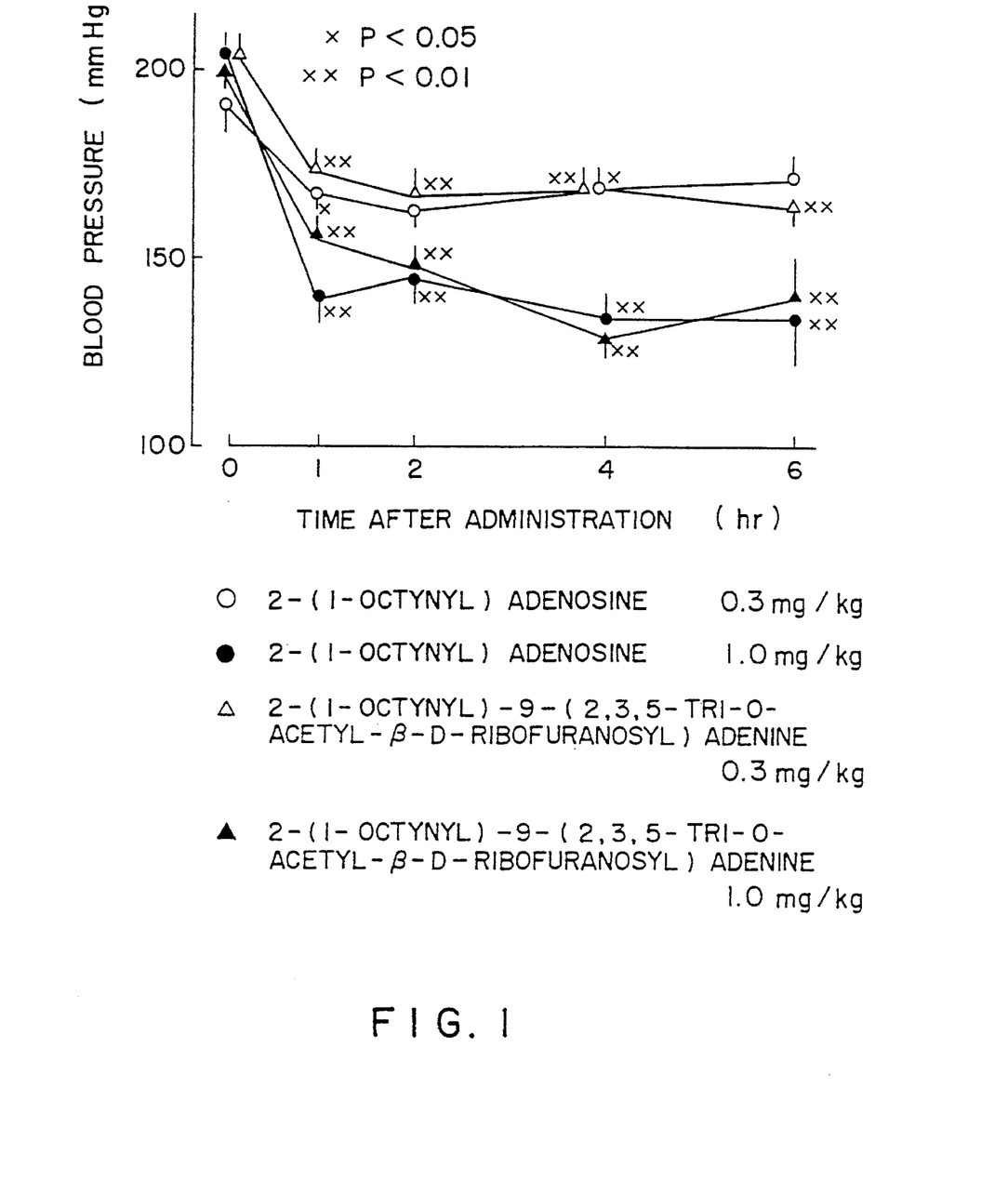

The results are shown in FIGURE 1. As will be apparent from FIGURE 1, 2-(1-octynyl)-9-(2,3,5-tri-O-acetyl-β -D-ribofuranosyl)adenine exhibits the same level of hypotensive effect as 2-(1-octynyl)adenosine.

Process for preparing 2-alkynyladenosine derivatives

Such 2-alkynyladenosine derivatives can be prepared by introducing an amino protecting group ordinarily used for the protection of an amino group and/or a hydroxyl protecting group ordinarily used for the protection of a hydroxyl group into at least one of the amino group at the 6-position and the hydroxy groups at 2', 3' and 5'-positions of the 2-alkynyladenosine. For example, in the case of a compound having acyl groups as the protective groups represented by $R^1$ through $R^4$, the compound can be prepared by reacting the compound represented by the following formula [VII]:

wherein $R^6$ represents a hydrogen atom or an amino protective group, and $R^7$, $R^8$, and $R^9$ represent a hydrogen atom or a hydroxyl protective group, and n is as defined above, with an acylating agent having acyl groups represented by $R^1$ through $R^4$.

Examples of the amino protecting group which is represented by $R^6$ in the above formula [VII] are carbonyl groups such as benzyloxycarbonyl, phenoxycarbonyl, and ethoxycarbonyl; and silyl groups such as trimethylsilyl, triethylsilyl, isopropyldimethylsilyl, tertbutyldimethylsilyl, and tertbutyldiphenylsilyl. Examples of the hydroxyl protecting groups represented by $R^7$, $R^8$, and $R^9$ are the aforementioned silyl groups and silyl groups such as tetraisopropyldisiloxanyl which can protect simultaneously two hydroxyl groups.

As the acylating agents used for the reaction, acid halides, acid anhydrides, mixed acid anhydrides (e.g., a product obtained by reacting a carboxylic acid and 2,4,6-triisopropylbenzenesulfonyl chloride or diethyl chlorophosphate) or activated esters (such as N-hydroxysuccinimide esters or N-hydroxyphthalimide esters) of a carboxylic acid having acyl groups represented by $R^1$ through $R^4$ can be used.

Examples of the reaction solvent which can be used are basic solvents such as trimethylamine, triethylamine, tributylamine,- pyridine, picoline, N-methylmorpholine, 2,6-lutidine, and diethylaniline; ether type solvents such as ethyl ether, tetrahydrofuran, and 1,4-dioxane; halogenated hydrocarbons such as methylene chloride, chloroform, and carbon tetrachloride; aromatic hydrocarbons such as benzene and toluene; amides such as N,N-dimethylformamide, N,N-dimethylacetamide, and formamide; nitriles such as acetonitrile; and dimethylaminopyridine, alone or as a mixture thereof.

The reaction can be carried out by reacting 1 mole of the compound [VII] with 1 to 10 moles of an acylating agent in a reaction solvent at a temperature of 0° to 50° C. for 1 to 20 hours.

With reference to the compound represented by the formula [V] wherein the acyl group is an acetyl group and/or a butyryl group, the reaction scheme for the preparation of the derivative of the present invention can be illustrated as follows:

wherein Ac represents an acetyl group; Bu represents a butyryl group; and n is as defined above.

According to the aforedescribed reaction scheme, the three derivatives (B), (C), and (D) of the present invention can be prepared from the 2-alkynyladenosine (A).

Also, in the case where the derivative of the present invention is a compound into which a protective group other than an acyl group has been introduced, the compound can be produced in a step in the course of the aforementioned process for producing 2-alkynyladenosines. That is, a product which is obtained by reacting a compound of the aforedescribed formula [I] with an aminating agent and which has the protective groups unremoved can be a derivative of the present invention having storage stability.

Furthermore, the derivative of the present invention of the formula [IV] wherein $R^1$, $R^2$, $R^3$ represent a hydroxyl protecting group, and $R^4$ represents a hydrogen atom can be also prepared by reacting the compound represented by the formula [VIII]:

[VIII]

wherein X represents an iodine atom or a bromine atom, and $R^1$, $R^2$, and $R^3$ are as defined above, with an alkyne represented by the formula [III]

$$HC\equiv C(CH_2)_nCH_3 \qquad [III]$$

wherein n is as defined above, in a reaction solvent in the presence of a palladium catalyst and a copper compound. In this connection, the reaction may be conducted in accordance with the conditions as employed in the conventional method for preparing 2-alkynyladenosines.

The derivatives of the present invention have, as described above, excellent storage stability. Thus, when 2-alkynyladenosines are required to be stored, the 2-alkynyladenosines may be converted into the compounds in this form, which are then stored in accordance with the method ordinarily used for the storage of organic compounds.

As a specific illustration of the storing method, the derivatives of the present invention, for example, in solid (crystalline or amorphous) form may be placed in an appropriate container such as a bottle, a bag, or a can and be stored under a temperature condition in the range from 0° C. to room temperature.

The derivatives of the present invention may be placed in the container in any of open, closed, airtight, and sealed states.

Furthermore, in order to prevent the decomposition of the derivatives of the present invention by light or oxygen, a light-shielding container such as a brown bottle is used as the container, and the residual oxygen may be substituted by an inert gas such as nitrogen gas.

The derivatives of the present invention may be converted into 2-alkynyladenosines only by removing the protective groups represented by $R^1$ through $R^4$ according to the ordinary way. For instance, when an acyl group has been used as the protective group, the derivatives of the present invention can be easily converted into 2-alkynyladenosines by subjecting the derivatives of the present invention to hydrolysis reaction.

The hydrolysis reaction can be carried out by the ordinary alkali treatment with methanolic ammonia, concentrated aqueous ammonia, sodium methoxide, sodium ethoxide, sodium hydroxide, potassium hydroxide or the like. As the reaction solvent, water or an alcohol such as methanol or ethanol can be used, and the reaction conditions can be appropriately selected from a reaction temperature in the range from 0° to 80° C. and a reaction time in the range from 10 minutes to 5 hours.

Example II-1

Synthesis of 2-(1-octynyl)-9-(2,3,5-tri-O-acetyl-β-D-ribofuranosyl)adenine (compound 1: in the formula [V],n =5, $R^4$=a hydrogen atom, $R^1=R^2=R^3$=an acetyl group):

In 20 ml of acetonitrile was suspended 0.90 g (2.4 mmole) of 2-(1-octynyl)adenosine, and 25 mg of 4-dimethytaminopyridine, 1.5 ml of triethylamine and 0.75 ml of acetic anhydride were added to the suspension. The mixture was stirred and caused to react at room temperature for 30 minutes. After the reaction, a small amount of methanol was added to the reaction solution, and the mixture was concentrated to dryness under reduced pressure. Ethyl acetate and water were added to the residue to form a solution, and the organic layer was then separated. The organic layer was washed with a saturated sodium bicarbonate solution, brine solution and water in this order, and then dried over anhydrous sodium sulfate. The organic layer was concentrated to dryness, and the residue was crystallized from methanol to obtain 1.1 g of 2-(1-octyl)-9-(2,3,5-tri-O-acetyl-β-D-ribofuranosyl)adenine as a colorless needle crystal (yield 91%).

Melting point 133° to 134° C.

IR spectrum (KBr): 2230 cm$^{-1}$ (C≡C)

Examples II-2 to 5

Synthesis of the derivatives of the present invention of the formula [V] (compound 2: n=3, $R^4$=a hydrogen atom, $R^1=R^2=R^3$=an acetyl group; compound 3: n=6, $R^4$=a hydrogen atom, $R^1=R^2=R^3$=an acetyl group; compound 4: n =7, $R^4$=a hydrogen atom, $R^1=R^2=R^3$=an acetyl group; compound 5: n =13, $R^4$ =a hydrogen atom, $R^1=R^2=R^3$=an acetyl group):

The reaction as in Example II-1 was conducted with an equal mole of 2-(1-hexynyl)adenosine (for the synthesis of compound 2), 2-(1-nonynyl)adenosine (for the synthesis of compound 3), 2-(1-decynyl)adenosine (for the synthesis of compound 4) and 2-(1-hexadecynyl)adenosine (for the synthesis of compound 5) in place of 2-(1-octynyl)adenosine to produce the objective compounds. The results are shown in Table 3.

The acetic anhydride in Example II-1 was replaced by an equal mole of benzoic anhydride to produce 1.14 g of 2-(1-octynyl)-9-(2,3,5-tri-O-benzoyl-β-D-ribofuranosyl)adenine (yield 69%).

Melting point: 105° to 109° C.

IR (KBr): 2230 cm$^{-1}$ (C≡C)

Examples II-8

Synthesis of $N^6$-n-butyryl-2-(1-octynyl)-9-(2,3,5-tri-O-acetyl-β -D-ribofuranosyl)adenine (compound 8: in the formula [V], n=5, $R^4$=a n-butyryl group, $R^1=R^2=R^3$=an acetyl group):

In 40 ml of pyridine was dissolved 2.5 g of 2-(1-octynyl)-9-(2,3,5-tri-O-acetyl-β-D-ribofuranosyl)adenine (compound 1), and 1.6 ml of n-butyryl chloride was added to the solution. The mixture was stirred and caused to react at 70° C. for 5 hours. After the reaction solution was cooled by leaving it to stand, it was concentrated to dryness, and the residue was extracted with ethyl acetate, washed with a saturated sodium bicarbonate solution and a brine solution in this order, and then dried over magnesium sulfate. After the organic layer was concentrated to dryness, the crystals formed were suspended in n-hexane and then collected by filtration to produce 1.6 g of $N^6$-n-butyryl-2-(1-octynyl)-9-(2,3,5-tri-O-acetyl-β -D-ribofuranosyl)adenine as a pale yellow needle crystal ( yield 56% ).

Melting point: 78° to 84° C.

IR spectrum (KBr): 2230 cm$^{-1}$ (C≡C)

Examples II-9

Synthesis of $N^6$-n-butyryl-2-(1-octynyl)-9-(β-D-ribofuranosyl)adenine (compound 9: in the formula IV], n =5, $R^4$=a n-butyryl group, $R^1=R^2=R^3$=a hydrogen atom):

In 50 ml of 1,4-dioxane was dissolved 1.38 g of $N^6$-n-butyryl- 2-(1-octynyl)-9-(2,3,5-tri-O-acetyl-β-D-ribofuranosyl)adenine (compound 8), and 50 ml of a 0.2N aqueous sodium hydroxide solution was added to the solution. The mixture was stirred and caused to react at room temperature for 25 minutes. After the reaction solution was neutralized with a 6N hydrochloric acid, it was concentrated to dryness, and the residue was extracted with chloroform. The chloroform layer was washed with a brine solution and then

TABLE 3

| Compound | Structure of Compound of the Formula [V] | | | | Yield | IR [KBr] cm$^{-1}$ | Melting Point |
|---|---|---|---|---|---|---|---|
| No. | n | $R^4$ | $R^1$ | $R^2$ | $R^3$ | (%) | (CC) | (°C.) |
| 2 | 3 | hydrogen | acetyl | acetyl | acetyl | 81 | 2230 | 124–125 |
| 3 | 6 | hydrogen | acetyl | acetyl | acetyl | 87 | 2230 | 96–99 |
| 4 | 7 | hydrogen | acetyl | acetyl | acetyl | 94 | 2230 | 99–101 |
| 5 | 13 | hydrogen | acetyl | acetyl | acetyl | 90 | 2230 | 103–104 |

Examples II-6

Synthesis of 2-(1-octynyl)-9-(2,3,5-tri-O-n-propionyl-β-D-ribofuranosyl)adenine (compound 6: in the formula [V], n=5, $R^4$=a hydrogen atom, $R^1=R^2=R^3$=a n-propionyl group):

The acetic anhydride in Example II-1 was replaced by an equal mole of n-propionic anhydride to produce 0.78 g of 2-(1-octynyl)-9-(2,3,5-tri-O-n-propionyl-β-D-ribofuranosyl)adenine (yield 60%).

Melting point: 85° to 87° C.

IR (KBr): 2230 cm$^{-1}$ (C≡C)

Examples II-7

Synthesis of 2-(1-octynyl)-9-(2,3,5-tri-O-benzoyl-β-D-ribofuranosyl)adenine (compound 7: in the formula [V], n =5, $R^4$=a hydrogen atom, $R^1=R^2=R^3$=a benzoyl group):

concentrated, and the residue obtained was purified by silica gel column chromatography (eluent: chloroform:methanol =6:1 (v/v)) and then crystallized from methanol-water to produce 0.73 g of $N^6$-n-butyryl-2-(1-octynyl)-9-(β-D-ribofurancsyl)adenine (yield 68%).

Melting point: 122° to 123° C.

IR spectrum (KBr): 2230 cm$^{-1}$ (C≡C)

Examples II-10 to 14

Synthesis of 2-(1-alkynyl)-9-(2,3,5-tri-O-acetyl-β-D-ribofuranosyl)adenine (in the formula [IV], n=3, 5, 10 or 13, $R^4$=a hydrogen atom, $R^1=R^2=R^3$=an acetyl group):

In 32 ml of dimethylformamide were suspended 1.62 g (3.12 mmole ) of 2-iodo-9-(2,3,5-tri-O-acetyl-β-D-ribofuranosyl)adenine, 38 mg of cuprous iodide and 67 mg of bis(triphenylphosphine)palladium dichloride, and 9 ml of triethylamine and 1.2 equivalent of an alkyne of the formula [III] were added to the suspension. The mixture was stirred and caused to react at 90° C. After the reaction, the solution was concentrated, and the residue was dissolved in chloroform. Hydrogen sulfide gas was then caused to flow through the chloroform solution for 1 minute.

After the gas flow was stopped, precipitates were removed by filtration, and the chloroform layer was concentrated. The residue obtained was purified by silica gel column chromatography (eluent: chloroform/methanol) to produce a 2-(1-alkynyl)-9-(2,3,5-tri-O-acetyl-β-D-ribofuranosyl)adenine having an alkynyl group corresponding to the alkyne used.

The results are shown in Table 4.

TABLE 4

| Alkyne- | Reaction Time (h) | Yield (%) | n in Product | Melting Point (°C.) |
|---|---|---|---|---|
| 1-Hexyne | 2 | 94 | 3 | 124–125 |
| 1-Octyne | 2 | 79 | 5 | 133–134 |
| 1-Nonyne | 4 | 82 | 6 | 96–99 |
| 1-Decyne | 14 | 64 | 10 | 99–101 |
| 1-Hexadecyne | 30 | 75 | 13 | 103–104 |

Application Example

In 50 ml of methanol was suspended 8.50 g of 2-(1-octynyl)- 9-(2,3,5-tri-O-acetyl-β-D-ribofuranosyl)adenine, and 87 mg of sodium methoxide was added to the suspension. The mixture was stirred and caused to react at room temperature for 1.5 hours.

After the reaction, the solution was neutralized by the addition of acetic acid and concentrated. The residue was then crystallized from an aqueous methanol solution to produce 5.84 g of 2-(1-octynyl)adenosine as a colorless needle crystal (yield 92.1%).

INDUSTRIAL APPLICABILITY

The present invention has solved the problems associated with the production and storage of the 2-alkynyladenosines produced by the conventional method by Matsuda et al. and, particularly, has developed novel synthetic intermediates useful for producing the 2-alkynyladenosines, a novel process for preparing the 2-alkynyladenosines with the use of the synthetic intermediates, novel 2-alkynyladenosine derivatives having excellent storage stability, and a method of storing the 2-alkynyladenosines with the use of the derivatives in this form. Therefore, the present invention can contribute extensively to the development of the 2-alkynyladenosines as medical agents.

What is claimed is:

1. A process for producing a 2-alkynyladenosine represented by the formula IV:

wherein n denotes an integer of 1 to 15, which process comprises reacting a compound represented by the formula II:

wherein $R^1$, $R^2$, $R^3$ and represent a hydrogen atom or a protective group, X represents a bromine atom or an iodine atom, and Y represents arylsulfonyloxy or chloro, with an alkyne represented by the formula III:

wherein n is as defined above, in a reaction solvent in the presence of a palladium catalyst to prepare a 2-alkynylpurine ribofuranoside derivative represented by the formula I:

wherein $R^1$, $R^2$, $R^3$, n and Y are as defined above, reacting the resulting 2-alkynylpurine ribofuranoside derivative with an aminating agent and then removing the protective groups, or removing the protective groups simultaneously with the reaction with the aminating agent.

2. A process for producing a 2-alkynyladenosine according to claim 1 wherein the reaction of the compound of the formula II and the compound of the formula III is conducted in the presence of a palladium catalyst and trace amounts of a copper compound.

3. A process for producing a 2-alkynyladenosine according to claim 1 wherein the reaction of the compound of the formula II and the compound of the formula III is conducted in the presence of a palladium catalyst and trace amounts of a copper compound, the amount of the copper compound being 0.02 mole or less to 1 mole of the compound represented by the formula II.

* * * * *